(12) United States Patent
Battaglia et al.

(10) Patent No.: US 8,474,323 B1
(45) Date of Patent: Jul. 2, 2013

(54) CARPET DEFLECTION MEASUREMENT DEVICE

(75) Inventors: Doug Battaglia, Gahanna, OH (US); Steve Adrian, London, OH (US); Jeffrey L. Driver, Dublin, OH (US)

(73) Assignee: Honda Motor Co., Ltd., Tokyo (JP)

( * ) Notice: Subject to any disclaimer, the term of this patent is extended or adjusted under 35 U.S.C. 154(b) by 710 days.

(21) Appl. No.: 12/551,761

(22) Filed: Sep. 1, 2009

(51) Int. Cl.
*G01N 19/06* (2006.01)

(52) U.S. Cl.
USPC .......................................................... 73/783

(58) Field of Classification Search
USPC .......................................................... 73/783
See application file for complete search history.

(56) References Cited

U.S. PATENT DOCUMENTS

| | | | |
|---|---|---|---|
| 2,376,814 A | 8/1943 | Robinson | |
| 3,470,737 A | 10/1969 | Fridley | |
| 3,805,599 A | 4/1974 | Illman et al. | |
| 4,004,457 A | 1/1977 | Eide et al. | |
| 4,096,742 A * | 6/1978 | Musolf et al. | 73/813 |
| 4,750,374 A | 6/1988 | Goss | |
| 4,972,719 A * | 11/1990 | Vinson et al. | 73/790 |
| 5,067,353 A | 11/1991 | Sersen | |
| 5,145,225 A * | 9/1992 | Muller et al. | 294/8.6 |
| 5,305,646 A | 4/1994 | Ashmore et al. | |
| 5,563,329 A | 10/1996 | Smith et al. | |
| 5,585,570 A * | 12/1996 | Raymond | 73/851 |
| 5,712,431 A * | 1/1998 | Vilendrer | 73/841 |
| 5,932,811 A | 8/1999 | Giebner | |
| 6,601,457 B2 | 8/2003 | Li et al. | |
| 6,931,942 B2 * | 8/2005 | Uhlik et al. | 73/853 |
| 7,159,850 B2 * | 1/2007 | Peters | 254/201 |
| 2008/0000285 A1 | 1/2008 | Gregory et al. | |

* cited by examiner

*Primary Examiner* — Lisa Caputo
*Assistant Examiner* — Octavia D. Hollington
(74) *Attorney, Agent, or Firm* — Rankin, Hill & Clark LLP

(57) ABSTRACT

A device for measuring rigidity, flexibility, and other properties associated with deformation of a thin planar material sample such as carpeting is described. The device is portable and can be manually operated. The device includes a movable testing assembly which is used to urge a testing member against a sample and measure compressive force(s) relative to deformation of the sample.

19 Claims, 5 Drawing Sheets

CARPET DEFLECTION MEASUREMENT DEVICE

FIELD OF INVENTION

The present invention relates to a device for measuring rigidity of carpeting or similar materials.

BACKGROUND OF THE INVENTION

In manufacturing and assembly environments, it is frequently desired to assess certain characteristics of materials such as carpeting or flexible panel-like materials in their installed state, partially installed state, or in an assembly environment. This presents several difficulties because most testing equipment is not mobile or designed for on-site use. In addition, many testing procedures are destructive in nature such that the sample undergoing testing is physically torn, severed, or otherwise altered. This is undesirable for testing of materials that have already been installed or are in an assembly environment and are about to be installed. Accordingly, a need exists for a portable and non-destructive device for measuring physical properties such as rigidity and flexibility of a thin planar member.

Testing carpet is typically performed by cutting or otherwise severing one or more samples from large carpet rolls. The cut pieces can then be subjected to an array of laboratory testing equipment. When attempting to use a portable device to measure or test certain characteristics of carpeting such as its flexibility or rigidity, a common problem is that measurements are not repeatable. That is, measurements can vary significantly between samples from the same source, and between different measurement trials. Accordingly, a need exists for a portable, hand-held device that can measure physical properties of carpeting in a consistent and repeatable manner.

SUMMARY OF THE INVENTION

The difficulties and drawbacks associated with previously known devices and measuring techniques are overcome in the present invention for a measurement device and related method of using the device. The device is particularly well suited for measuring carpet stiffness.

In one aspect, the present invention provides a measurement device for measuring force associated with a material deflection. The device comprises a frame; a material supporting fixture supported by the frame, the fixture defining a rest plane for contacting and supporting a material to be measured; and a testing assembly supported by the frame. The testing assembly includes a testing member in communication with a force gauge. The testing member is positionable between a material deflection position and a retracted position. The rest plane defined by the fixture lies between the material deflection position and the retracted position.

In another aspect, the present invention provides a device for measuring properties associated with deforming a thin planar material sample. The device comprises a frame including a main member and a first leg extending therefrom. The first leg defines a distal end. The device also comprises a second leg pivotally attached to the frame. The second leg also defines a distal end. The device also comprises a handle pivotally attached to the frame and in operable engagement with the second leg such that upon pivoting of the handle, the second leg also pivots. The device further comprises a material supporting fixture affixed to the distal end of the first leg. The fixture of the device includes a circular hoop. The hoop defines a face for contacting and supporting a thin planar material sample. The face of the hoop extends within a rest plane. The device further comprises a testing assembly affixed to the distal end of the second leg. The testing assembly includes a testing member and a force gauge. The testing member is positionable between a retracted position and an extended position. The rest plane extends between the retracted position and the extended position.

In yet another aspect, the present invention provides a method for measuring force associated with a material deflection. The method comprises providing a device including a frame, a material supporting fixture supported by the frame, the fixture defining a rest plane for contacting and supporting a material to be measured, and a positionable testing assembly supported by the frame. The testing assembly includes a testing member in communication with a force gauge. The method further comprises positioning a material to be tested in contact with the fixture and generally oriented in the rest plane. And, the method comprises moving the testing member from a retracted position into contact with the material and further to a material deflection position. Upon positioning the testing member to a material deflection position, a compressive force applied to the testing member is measured by the force gauge.

As will be realized, the invention is capable of other and different embodiments and its several details are capable of modifications in various respects, all without departing from the invention. Accordingly, the drawings and description are to be regarded as illustrative and not restrictive.

DETAILED DESCRIPTION OF THE EMBODIMENTS

Figure 1:
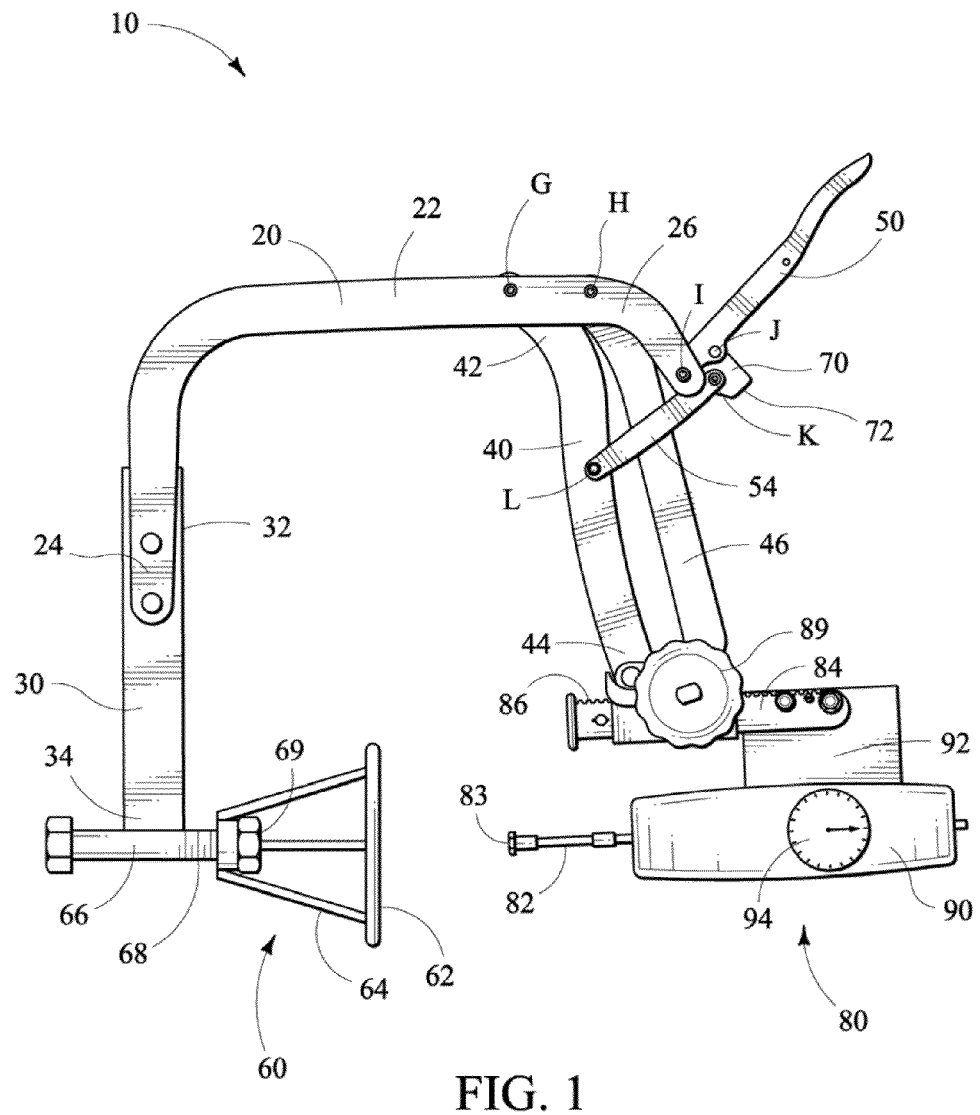
FIG. 1 is a schematic illustration of a preferred embodiment device in accordance with the present invention, the device shown in a retracted position.

The present invention provides a measurement device that is particularly well suited for measuring carpet deflection. Carpet deflection measurements provide a quantitative value that relates a particular dimensional deflection value to a corresponding force value. Thus, for example, the present invention device can be used to measure the amount of compressive force applied to a sample of carpet which is required to deflect the carpet 20 mm beyond a flat circular ring. These measurements can be used in comparing different carpet types or comparing properties of a single carpet type at different conditions such as across changing temperatures.

Generally, the preferred embodiment measurement device includes a frame, a material supporting fixture affixed to the frame for supporting a sample to be tested, and a testing assembly supported by the frame. The testing assembly includes a force gauge and is positionable with respect to the fixture. The fixture includes a circular ring against which the carpet to be tested is positioned. During testing, the carpet sample is placed between the circular ring of the fixture and the testing assembly. The testing assembly is urged against the carpet to cause the carpet to be deflected at least partially through the ring. A corresponding force measurement is then noted by referring to the force gauge. Each of the main components of the preferred embodiment measurement device is described in greater detail as follows.

Frame

The frame is preferably a rigid member or collection of rigid members, such as may be formed from metal for example, steel or aluminum. The frame may be provided in a variety of different shapes, sizes, and configurations. However, it is generally preferred that the frame includes a longitudinal main member and at least one leg extending outward therefrom and preferably, from an end of the main member. The leg can extend from the main member at nearly any angle, however a transverse orientation is preferred. It is also preferred that the leg be rigidly attached to the main member, however the invention includes variations in which the leg is movable with respect to the main member.

Preferably, a second leg also extends from the main member. This second leg is preferably pivotally attached to the main member. The second leg preferably pivots within the same plane within which lies the main member and the first leg. The second leg pivots between a retracted position in which the distal end of the second leg is farthest from the first leg, and an extended position in which the distal end of the second leg is closest to the first leg. The second leg is preferably attached to the main member at an end of the main member opposite the end to which the first leg is attached. The second leg supports the testing assembly, described in greater detail herein.

The second leg pivots about a pivot angle of about 5° to about 30° or more. That is, the pivot angle is the angle extending between the retracted position and the extended position of the second leg. The second leg is preferably engaged with a handle to facilitate pivoting the second leg. The handle is also preferably pivotally attached to the main member and proximate the location at which the second leg is attached to the main member. The handle can be operably engaged with the second leg by one or more straps or other connectors. The present invention includes the use of additional pivoting leg members generally extending alongside the second leg member. These additional pivoting leg member(s) can serve to provide further support for the testing assembly affixed at a distal end of the second leg.

The present invention preferably includes a force amplification assembly. That is, it is preferred that such assembly be used to increase and/or govern the amount of force exerted by the pivotable second leg as a result of force application by the handle. Such assembly can be used to provide a specific motion profile for the testing assembly attached at a distal end of the second leg, as the handle is pivoted from one position to another. An example of such a force amplification and/or force governing assembly is a cam assembly and lever arrangement. In such example, the handle can be pivotally attached to a cam element which in turn is pivotally attached to the frame. The cam element can contact an engagement surface of a pivotable member and thereby govern movement of that member.

The legs, handle, and other frame components are preferably formed from steel, aluminum, or other rigid materials.

Material Supporting Fixture

As noted, the material supporting fixture is preferably attached to a distal end, or substantially so, of the first leg member of the frame. The material supporting fixture preferably includes a ring or circular hoop against which a sample to be tested is positioned. The fixture is directed toward the testing assembly, and preferably such that the center of the ring is aligned with a testing member of the testing assembly. Additional details as to the preferred orientation of the ring and testing assembly are described later herein.

The fixture can be formed from a wide array of materials, however metals such as steel and aluminum are preferred. A wide array of sizes for the material supporting fixture may be used. Although not wishing to be limited to any particular size, it has been found that a circular hoop having an inner diameter of about 110 mm and an outer diameter of about 120 mm is preferred.

The fixture is also preferably positionable with respect to the first leg of the frame. That is, it is preferred that the fixture be selectively positionable and adjustable in at least one direction, i.e. preferably towards or away from the testing assembly. Various mechanical assemblies such as threaded fasteners can be used to provide this adjustable feature.

Testing Assembly

The testing assembly is preferably affixed to a distal end of the pivotable second leg such that upon pivoting the second leg, the testing assembly is positioned closer to, or further from, the fixture.

The testing assembly includes a force gauge and a testing member in engagement with the force gauge. The force gauge can utilize electronic force measuring means, mechanical force measuring means, or both. Preferably, the force gauge measures compressive forces applied to the testing member. The force gauge preferably includes a dial display or can utilize a digital display. It is also contemplated that the force gauge could transmit information pertaining to the measured force(s) to a display device external to the measurement device. A preferred force gauge is a Force Dial Model FDL available from Wagner Instruments of Greenwich, Conn. A typical preferred force range for the gauge is 10 KgF×0.05 KgF.

The testing assembly is preferably adjustably affixed to a distal end of the pivotable second leg. By adjusting the position of the testing assembly, and in particular, of the force gauge to the second leg, the relative position of the force gauge to the fixture can be changed as desired. This is particularly desirable since this feature provides positional adjustment of the force gauge relative to the fixture when the device is in an extended position.

Preferred Device

Figure 2:
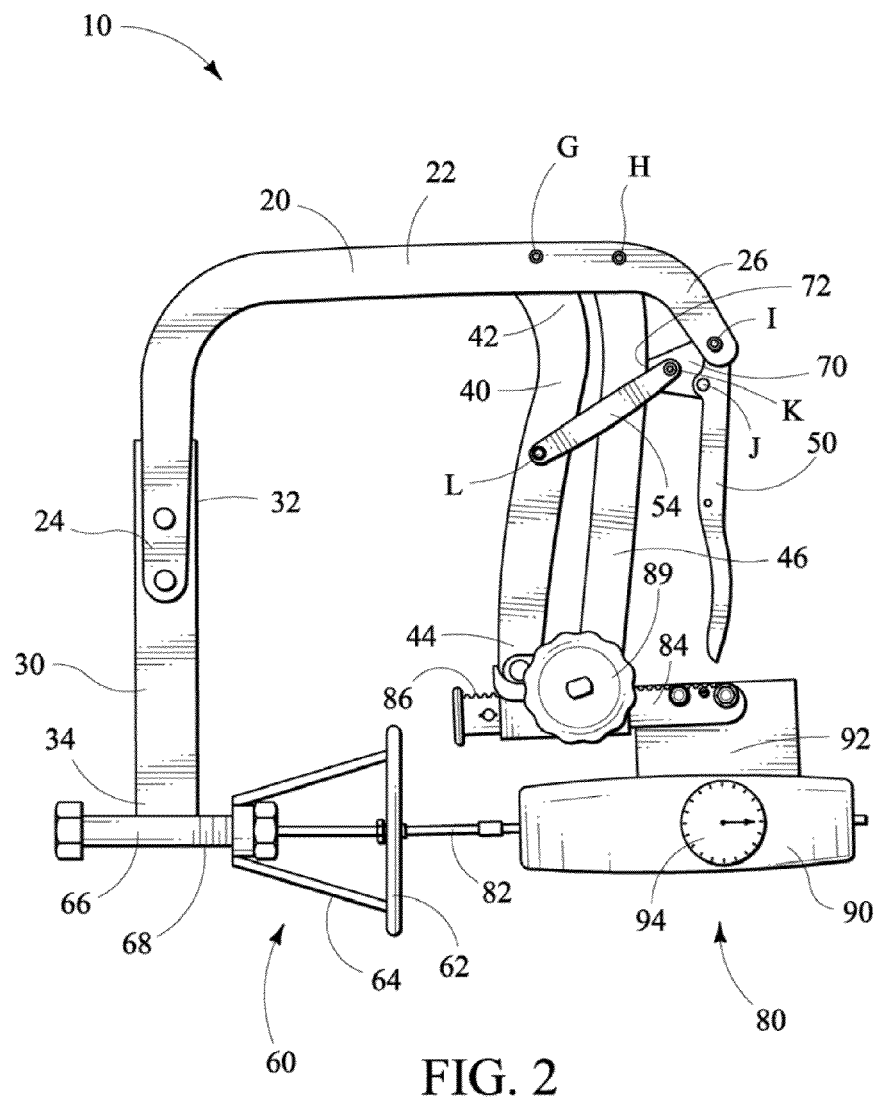
FIG. 2 is a schematic illustration of the preferred embodiment device in an extended position.

FIGS. 1-6 illustrate a preferred embodiment measurement device 10 in accordance with the present invention. Specifically, as shown in FIGS. 1 and 2, the device 10 comprises a frame 20, a fixture 60, and a testing assembly 80. FIG. 1 illustrates the device in a retracted position, such as prior to a testing or measuring operation. And, FIG. 2 illustrates the device in an extended position, such as during a testing or measuring operation. The frame 20 generally includes a longitudinal main member 22 defining first and second ends 24 and 26, respectively. Preferably affixed to the first end 24 of the main member 22 is a first leg 30. And, the frame 20 includes a second leg 40 pivotally attached to the main member 22 proximate the second end 26 of the main member 22. The second leg 40 is preferably pivotally attached to the main member 22 at member G. The resulting assembly of the main member 22, the first leg 30, and the second leg 40 is preferably in the form of a U-shape, with the member 22 and legs 30 and 40 all co-planar with one another or at least substantially so. Although the frame 20 is depicted in FIG. 1 as including a transversely extending section that terminates at the first end 24, to which the first leg 30 is attached, it will be appreciated that the present invention includes versions in which the main member 20 does not include the noted transversely extending section and instead, includes a first leg that is longer in length than the leg 30 depicted in FIG. 1. Furthermore, it is contemplated that the main member 22 and the first leg 30 could be integrally formed with one another.

Figure 3:
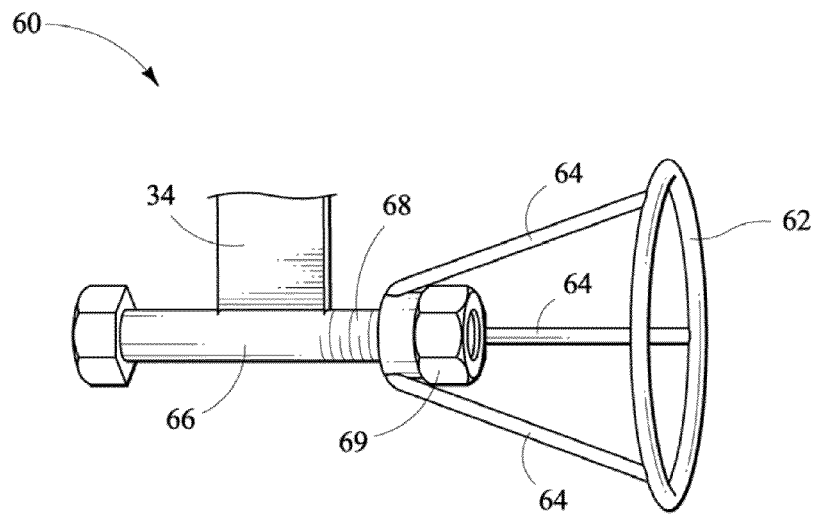
FIG. 3 is a detailed view of a material supporting fixture portion of the device.

Referring further to FIGS. 1, 2, and 3, the first leg 30 defines a first end 32 which is attached, affixed or otherwise formed with the main member 22. The leg 30 defines a second end 34, opposite the first end 32. Attached proximate the second end 34 of the first leg 30, is the fixture 60. The fixture 60 comprises a circular ring or circular hoop 62, a base 66 secured to the second end 34 of the leg 30, and one or more support members 64 extending between the ring 62 and the base 60. It will be appreciated that the present invention includes the use of a variety of different structures and assemblies for supporting the ring 62. Preferably, the ring 62 is positionally adjustable with respect to the frame 20 and its components. The preferred embodiment device 10 includes a positioning assembly which provides for selective adjustment of the position of the ring 62 relative to the end 34 of the leg 30. A wide array of different positioning assemblies may be used to achieve such selective adjustment. A preferred assembly is the provision of a region of threads along a circular shaft 68, which is threadedly engaged with a nut 69 or other threaded fastener. The nut 69 is secured or otherwise attached to the ring 62 and/or the support members 64. Thus, by rotating the ring 62, support members 64, and nut 69 about the longitudinal axis of the threaded shaft 68, the linear position of the ring 62 relative to the frame 20 can be selectively adjusted. The present invention includes an array of other types of positioning assemblies besides that depicted in the referenced figures.

Figure 4:
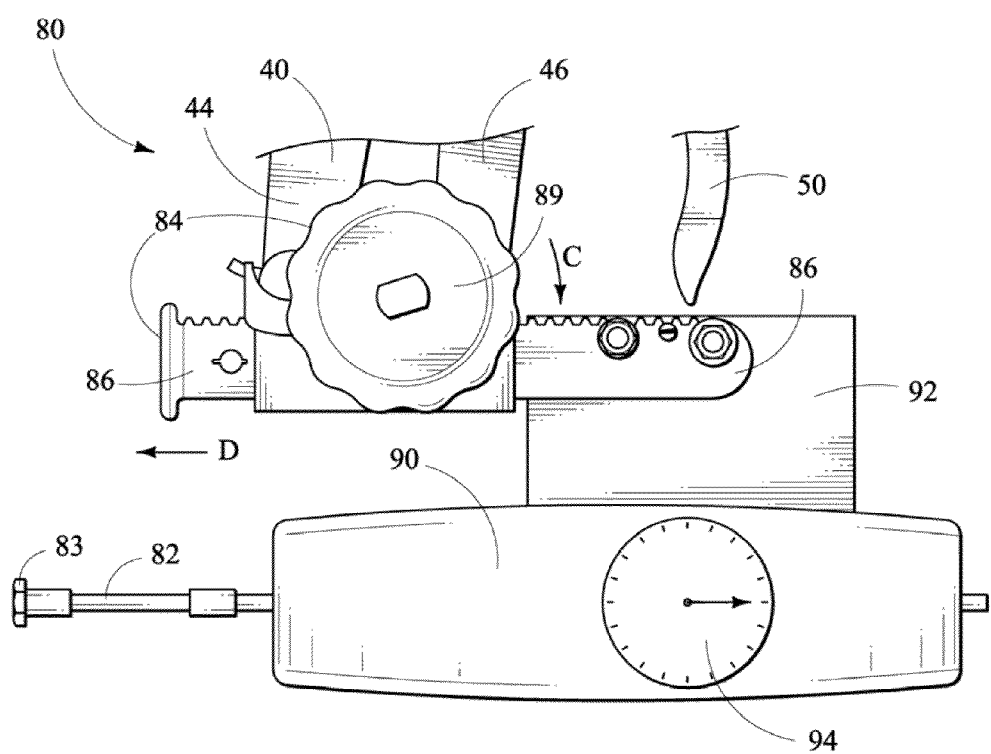
FIG. 4 is a detailed view of a testing assembly portion of the device.

Referring to FIGS. 1, 2, and 4, the device 10 preferably also comprises the testing assembly 80. The testing assembly 80 is affixed to a distal end of the second leg 40. The second leg 40 defines a first proximal end 42 and an opposite, distal, second end 44. The testing assembly 80 is preferably attached or otherwise affixed to the second end 44 of the second leg 40, which can be pivoted about its point of attachment G to the frame 20. The testing assembly 80 includes a force gauge 90 and a testing member 82 generally extending therefrom, the member 82 defining a distal end 83. The force gauge 90 includes a dial 94 or other display for providing information concerning the amount of force applied to the testing member 82. As explained in greater detail herein, during a testing or measuring operation, the distal end 83 of the testing member 82 contacts the carpeting or other planar sample undergoing testing. The testing assembly 80 also includes a positioning assembly 84, which preferably utilizes a rack and pinion geared configuration such that rotation of an actuator 89 causes linear movement of a toothed rack member 86. For example, referring to FIG. 4, rotation of the actuator 89 in the direction of arrow C causes linear movement of the rack member 86 in the direction of arrow D. The force gauge 90 is preferably affixed to the positioning assembly 84 and most preferably affixed to the rack member 86 by a support arm 92. It will be appreciated that a wide array of other affixment assemblies and configurations could be utilized.

Referring to FIGS. 1 and 2, the preferred embodiment device 10 also includes a handle 50. The handle 50 is preferably movably attached to the frame 20. The handle 50 and its attachment and/or configuration with the frame 20 and the second leg 40 is preferably such that pivoting of the handle 50 causes pivoting motion of the second leg 40 and movement of the testing assembly 80 between extended and retracted positions. Although a wide array of different mechanisms and assemblies can be used to achieve this configuration, a preferred assembly is depicted in the referenced figures. Referring to FIGS. 1 and 2, the device 10 preferably includes a stop cam element 70. The third leg 46 is preferably pivotally engaged with the main member 22 of the frame 20 at member H. The third leg 46 generally extends in a parallel fashion with the second leg 40. The distal end of the third leg 46 is preferably engaged to the positioning assembly 84 of the testing assembly 80. The handle 50 is secured to the cam element 70 at member J, and also secured to the main member 22 at member I. The cam element 70 is rotatably attached to the main member 22 and preferably proximate the second end 26 of the main member 22 by member I. Thus, upon movement of the handle 50 and the cam element 70, the cam element 70 also pivots about member I. Movement of the cam element 70 is transmitted to the second leg 40 by a connecting member 54 extending between the cam element 70 and the second leg 40. The connecting member 54 is affixed to the second leg 40 by member L and affixed to the cam element 70 by member K. Preferably, the cam element 70 includes a stop surface 72 defined along a side of the cam element 70. Upon positioning the handle 50 as shown in FIG. 2 from the position illustrated in FIG. 1, the stop surface 72 contacts the third leg 46 and prevents further displacement of the handle 50.

Figure 5:
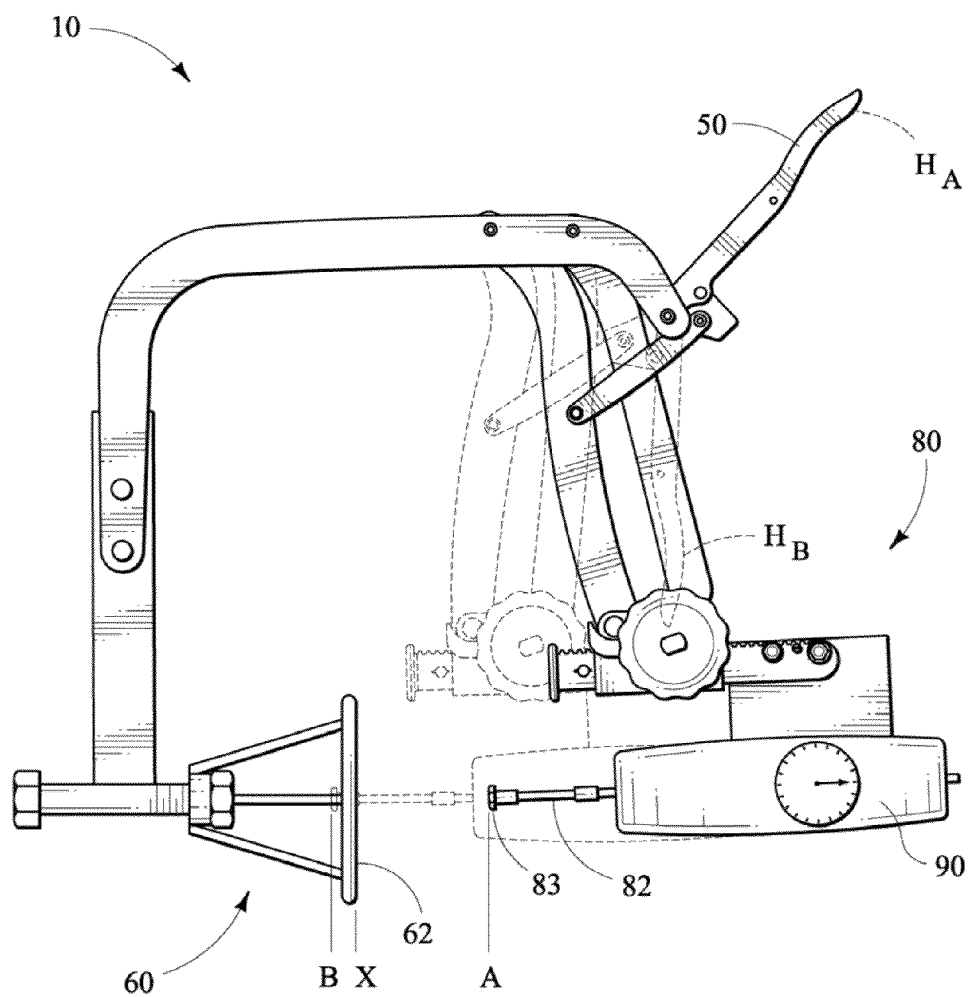
FIG. 5 is a view further illustrating relative positions of the device in retracted and extended positions.

FIG. 5 further illustrates the device 10 in a fully retracted position indicated by the testing assembly 80 and handle 50 shown in solid lines, and the handle shown in position $H_A$. In this retracted position, the distal end 83 of the testing member 82 is in position A. In an extended position, shown by the components 80, 50, and others in dashed lines, the handle 50 is in position $H_B$ and the distal end 83 of the testing member 82 is in position B. It will be noted that a plane X of orientation of the ring 62 is between position A and position B.

Figure 6:
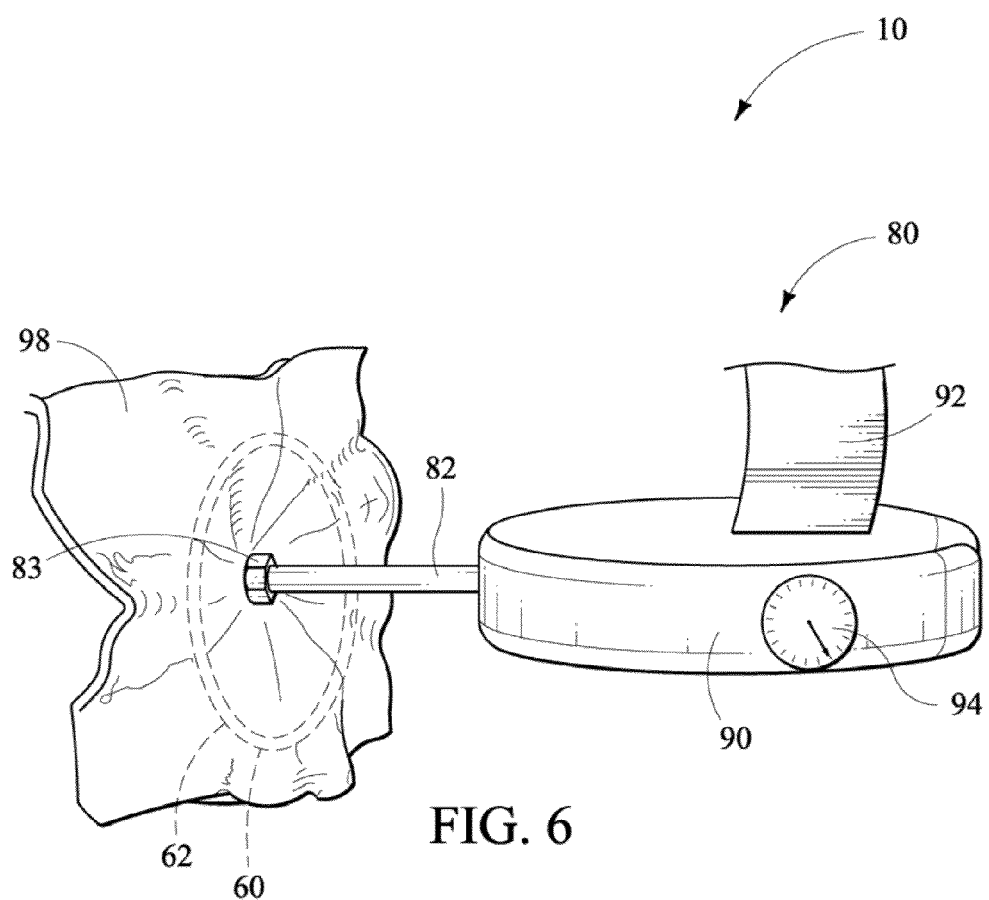
FIG. 6 illustrates measuring rigidity of a material sample using the preferred embodiment device.

FIG. 6 schematically illustrates a portion of the preferred device 10 in contact with a sample 98 undergoing a deflection measurement operation. Specifically, a portion of the sample 98 is in contact with the ring 62 of the fixture 60. The testing assembly 80 including the force gauge 90 is positioned toward the sample 98, and such that the distal end 83 of the testing member 82 is in contact with the sample 98. The testing assembly 80 and the force gauge 90 are progressively urged against the sample 98 until a desired amount of deflection of the sample occurs, at which point the corresponding compressive force exerted on the testing member 82 is indicated by a dial 94 or other indicator associated with the force gauge 90.

Methods

The present invention provides a method for measuring force associated with a material deflection, such as the amount of deflection associated with a particular force. The method generally comprises providing a device including a frame, a material supporting fixture supported by the frame, the fixture defining a rest plane for contacting and supporting a material to be measured, and a positionable testing assembly supported by the frame. The testing assembly includes a testing member in communication with a force gauge. The method further comprises positioning a material to be tested in contact with the material supporting fixture and generally oriented in the rest plane. And, the method comprises moving the testing member from a retracted position into contact with the material and further to a material deflection position, the rest plane extending between the retracted position and the material deflection. Upon positioning the testing member to a material deflection position, a compressive force applied to the testing member is measured by the force gauge. This method enables quick and convenient measurement of carpet deflection values. It has been discovered that the measurement techniques described herein using the preferred device provide consistent and repeatable measurement values.

More specifically, when measuring a carpet sample, it is preferred to place the carpet sample on a level surface, carpet side directed upwards. The compression depth of the device is adjusted to 15 mm, for example. The compression depth is the distance that the distal end of the testing member extends through the circular hoop of the fixture. The force gauge is zeroed and set to a mode in which the peak force measured is noted, sometimes referred to as "peak hold". The device is then positioned over the carpet sample. The sample is contacted with the hoop of the fixture, and the testing assembly then urged toward the carpet sample. The operator continues to move the testing member against the carpet sample, i.e. by moving the handle of the device, until the compression depth of the device is reached. Care should be taken so as to not introduce significant movement of the device and carpet sample. The peak force measured is then noted. The procedure may be repeated as desired, such as on different regions of the carpet.

It will be appreciated that the present invention includes variations of the previously described preferred embodiment device 10. For example, the invention includes the use of different positioning members, different camming assemblies, different handle provisions, different testing assemblies, and includes variations in the described structures for the material supporting fixture, frame, and testing assembly.

Many other benefits will no doubt become apparent from future application and development of this technology.

As described hereinabove, the present invention solves many problems associated with previous type devices and measuring methods. However, it will be appreciated that various changes in the details, materials and arrangements of parts, which have been herein described and illustrated in order to explain the nature of the invention, may be made by those skilled in the art without departing from the principle and scope of the invention, as expressed in the appended claims.

What is claimed is:

1. A measurement device for measuring force associated with a material deflection, the device comprising:
   a frame;
   a material supporting fixture supported by the frame, the fixture defining a rest plane for contacting and supporting a material to be measured, wherein the fixture includes a material sample supporting circular hoop; and
   a testing assembly supported by the frame, the assembly including a testing member in communication with a force gauge, the testing member positionable between a material deflection position and a retracted position, wherein the rest plane lies between the material deflection position and the retracted position and wherein the force gauge measures a compressive force applied to the testing member when the testing member is moved from the retracted position into contact with the material and into the material deflection position.

2. The device of claim 1 wherein the hoop is oriented within a plane transverse to the direction of movement of the testing member.

3. The device of claim 1 wherein the testing member defines a longitudinal axis, the longitudinal axis of the testing member being oriented along a line extending through the center of the hoop.

4. A measurement device for measuring force associated with a material deflection, the device comprising:
   a frame;
   a material supporting fixture supported by the frame, the fixture defining a rest plane for contacting and supporting a material to be measured; and
   a testing assembly supported by the frame, the assembly including a testing member in communication with a force gauge, the testing member positionable between a material deflection position and a retracted position, wherein the rest plane lies between the material deflection position and the retracted position and wherein the force gauge measures a compressive force applied to the testing member when the testing member is moved from the retracted position into contact with the material and into the material deflection position and wherein the frame includes a main body member, a first leg member transversely extending from the main body member, a second leg member extending from the main body member and pivotally attached thereto, the material supporting fixture affixed to the first leg member, the testing assembly affixed to the second leg member, the fixture and the testing assembly being disposed in operable engagement with one another.

5. The device of claim 4 further comprising:
   a handle pivotally attached to the main body member of the frame and in operable engagement with the second leg member such that pivoting of the handle causes pivoting of the second leg member relative to the main body member of the frame.

6. The device of claim 4 wherein the second leg member extends between the frame and the testing assembly, the testing assembly being affixed to a distal end of the second leg member.

7. The device of claim 6 wherein the testing assembly is selectively positionable with respect to the distal end of the second leg member.

8. The device of claim 4 wherein the material supporting fixture is affixed to a distal end of the first leg member, the fixture including a circular hoop.

9. The device of claim 8 wherein the hoop is selectively positionable with respect to the distal end of the first leg member.

10. A device for measuring properties associated with deforming a thin planar material sample, the device comprising:
    a frame including a main member and a first leg extending therefrom, the first leg defining a distal end;
    a second leg pivotally attached to the frame, the second leg defining a distal end;
    a handle pivotally attached to the frame and in operable engagement with the second leg such that upon pivoting of the handle, the second leg also pivots;
    a material supporting fixture affixed to the distal end of the first leg, the fixture including a circular hoop, the hoop defining a face for contacting and supporting a planar material sample, the face extending within a rest plane; and
    a testing assembly affixed to the distal end of the second leg, the testing assembly including a testing member and a force gauge;

wherein the testing member is positionable between a retracted position, and an extended position, the rest plane extending between the retracted position and the extended position.

11. The device of claim 10 wherein the testing assembly is positioned to the extended position by pivoting the handle relative to the frame, thereby displacing the testing member.

12. The device of claim 10 wherein the hoop is positionable relative to the distal end of the first leg.

13. The device of claim 10 wherein the testing assembly is positionable relative to the distal end of the second leg.

14. A method for measuring force associated with a material deflection, the method comprising:
providing a device including a frame, a material supporting fixture supported by the frame, the fixture defining a rest plane for contacting and supporting a material to be measured, and a positionable testing assembly supported by the frame, the testing assembly including a testing member in communication with a force gauge, and wherein the frame includes a main body member, a first leg member transversely extending from the main body member, a second leg member extending from the main body member and pivotally attached thereto, the material supporting fixture affixed to the first leg member, the testing assembly affixed to the second leg member, the fixture and the testing assembly being disposed in operable engagement with one another;
positioning a material to be tested in contact with the fixture and generally oriented in the rest plane;
moving the testing member from a retracted position into contact with the material and further to a material deflection position, the rest plane extending between the retracted position and the material deflection position, wherein upon positioning of the testing member to the material deflection position, a compressive force applied to the testing member is measured by the force gauge.

15. The method of claim 14 wherein the material supporting fixture includes a material sample supporting circular hoop, the hoop defining a face lying within the rest plane.

16. The method of claim 15 wherein during moving the testing member, a distal end of the testing member is moved through the center of the hoop.

17. The method of claim 14 wherein the material to be tested is carpeting.

18. A measurement device for measuring force associated with a material deflection, the device comprising:
a frame including a longitudinal main body member, a first leg member transversely extending from the main body member, and a second leg member extending from the main body member and pivotally attached thereto, the second leg pivotable between a retracted position and a material deflection position;
a material supporting fixture supported by the frame, the fixture affixed to the first leg member and defining a rest plane for contacting and supporting a material to be measured, the rest plane interposed between the material deflection position and the retracted position; and
a testing assembly supported by the frame and affixed to the second leg member, the testing assembly including a testing member in communication with a force gauge, the testing member movable with the second leg between the material deflection position and the retracted position, wherein the testing assembly and the fixture are both disposed in operable engagement with one another.

19. The device of claim 18 wherein the material supporting fixture includes a hoop, the hoop oriented within a plane transverse to the direction of movement of the testing member.

* * * * *